US00PP27653P3

(12) United States Plant Patent
Charlesworth et al.

(10) Patent No.: US PP27,653 P3
(45) Date of Patent: Feb. 7, 2017

(54) ***LAVANDULA* PLANT NAMED 'DOWPHSCNT'**

(50) Latin Name: *Lavandula intermedia*
Varietal Denomination: DOWPHSCNT

(71) Applicants: Simon Charlesworth, Tonbridge (GB); Fiona Wilson, Aylesford (GB)

(72) Inventors: Simon Charlesworth, Tonbridge (GB); Fiona Wilson, Aylesford (GB)

( * ) Notice: Subject to any disclaimer, the term of this patent is extended or adjusted under 35 U.S.C. 154(b) by 58 days.

(21) Appl. No.: 14/545,497

(22) Filed: May 11, 2015

(65) Prior Publication Data

US 2016/0338254 P1 Nov. 17, 2016

(51) Int. Cl.
*A01H 5/02* (2006.01)

(52) U.S. Cl.
USPC ..... Plt./445

(58) Field of Classification Search
USPC ..... Plt./445
See application file for complete search history.

(56) References Cited

PUBLICATIONS

UPOV hit on *lavandula* plant named 'DOWPHSCNT,' QZ PBR 20141315, published Aug. 15, 2015.*
Internet article "Heavenly Lavender", http://heavenlylavender.com/?p=24, published May 18, 2014.*

* cited by examiner

*Primary Examiner* — Anne Grunberg
(74) *Attorney, Agent, or Firm* — Cassandra Bright

(57) ABSTRACT

A new and distinct Lavender cultivar named 'DOWPHSCNT' is disclosed, characterized by short, compact plants. Plants produce unique short, wide flower spikes, uniform inflorescence and very compact plant form. The new variety is a *Lavandula*, normally produced as an outdoor garden or container plant.

2 Drawing Sheets

Figure 1:
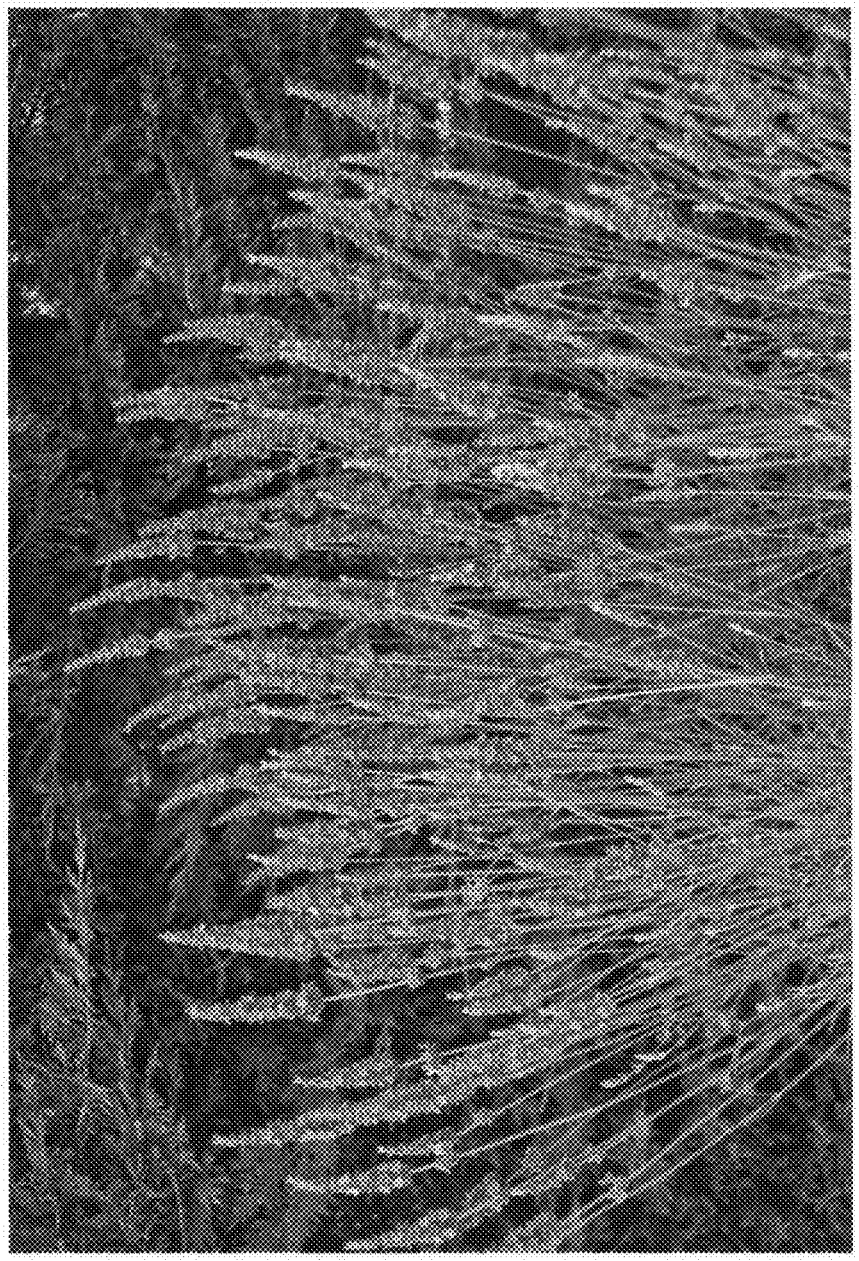

Latin name of the genus and species: *Lavandula intermedia.*

Variety denomination: 'DOWPHSCNT'.

BACKGROUND OF THE INVENTION

The new *Lavandula* cultivar is a product of a planned breeding program conducted by the inventors, Simon Charlesworth and Fiona Wilson, in Kent, the United Kingdom. The objective of the breeding program was to produce new Lavender varieties for ornamental commercial applications.

The parent variety is the, unpatented commercial variety *Lavandula* 'Abrialii'. Plants of the parent variety were treated to induce mutation. Cuttings from the treated plants were selected, propagated and plants observed for noticeable differences from the parent variety.

Asexual reproduction of the new cultivar was performed by vegetative cuttings. This was first performed in Kent, the United Kingdom during 2009. Subsequent propagation has shown that the unique features of this cultivar are stable and reproduced true to type in multiple successive generations.

SUMMARY OF THE INVENTION

The cultivar 'DOWPHSCNT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DOWPHSCNT' These characteristics in combination distinguish 'DOWPHSCNT' as a new and distinct Lavender cultivar:

1. Compact plant.
2. Short plants with a moderate growth rate.
3. Broad foliage.
4. Short flower spikes.
5. Wide floral calyces.

Plants of the new cultivar 'DOWPHSCNT' are similar to plants of the parent variety in most horticultural characteristics, however, plants of the new cultivar 'DOWPHSCNT' differ in the following;

1. Shorter plant height.
2. Broader foliage.
3. Shorter flower heads with wider calyces.

COMMERCIAL COMPARISON

Plants of the new cultivar 'DOWPHSCNT' are comparable to the unpatented commercial variety *Lavandula intermedia* 'Provence'. The two Lavender varieties are similar in most horticultural characteristics; however, the new variety 'DOWPHSCNT' differs in the following:

1. Plants of the new variety are at least 20% smaller in height and width.
2. Flower spikes of the new variety are shorter, approximately 8 cm compared to 18 cm.
3. Flower spikes of the new variety are wider, approximately 2 cm compared to 1 cm.

Plants of the new cultivar 'DOWPHSCNT' can also be comparable to the unpatented commercial variety *Lavandula* 'Grosso'. The two Lavender varieties are similar in most horticultural characteristics; however, the new variety 'DOWPHSCNT' differs in the following:

1. Plants of the new variety are approximately shorter, approximately 60 cm at maturity compared to 90 cm mature height of this comparator.
2. Flower spikes of the new variety are shorter, approximately 8 cm compared to 18 cm.
3. Flower spikes of the new variety are wider, approximately 2 cm compared to 1.5 cm.
4. Flower color of the new variety is lighter than flower color of this comparator.

BRIEF DESCRIPTION OF THE PHOTOGRAPHS

The accompanying photograph in FIG. 1 illustrates in full color a typical plant of 'DOWPHSCNT' grown outdoors, in the ground in Kent, England. Age of the plant photographed is approximately 4 years from a rooted cutting.

Figure 2:
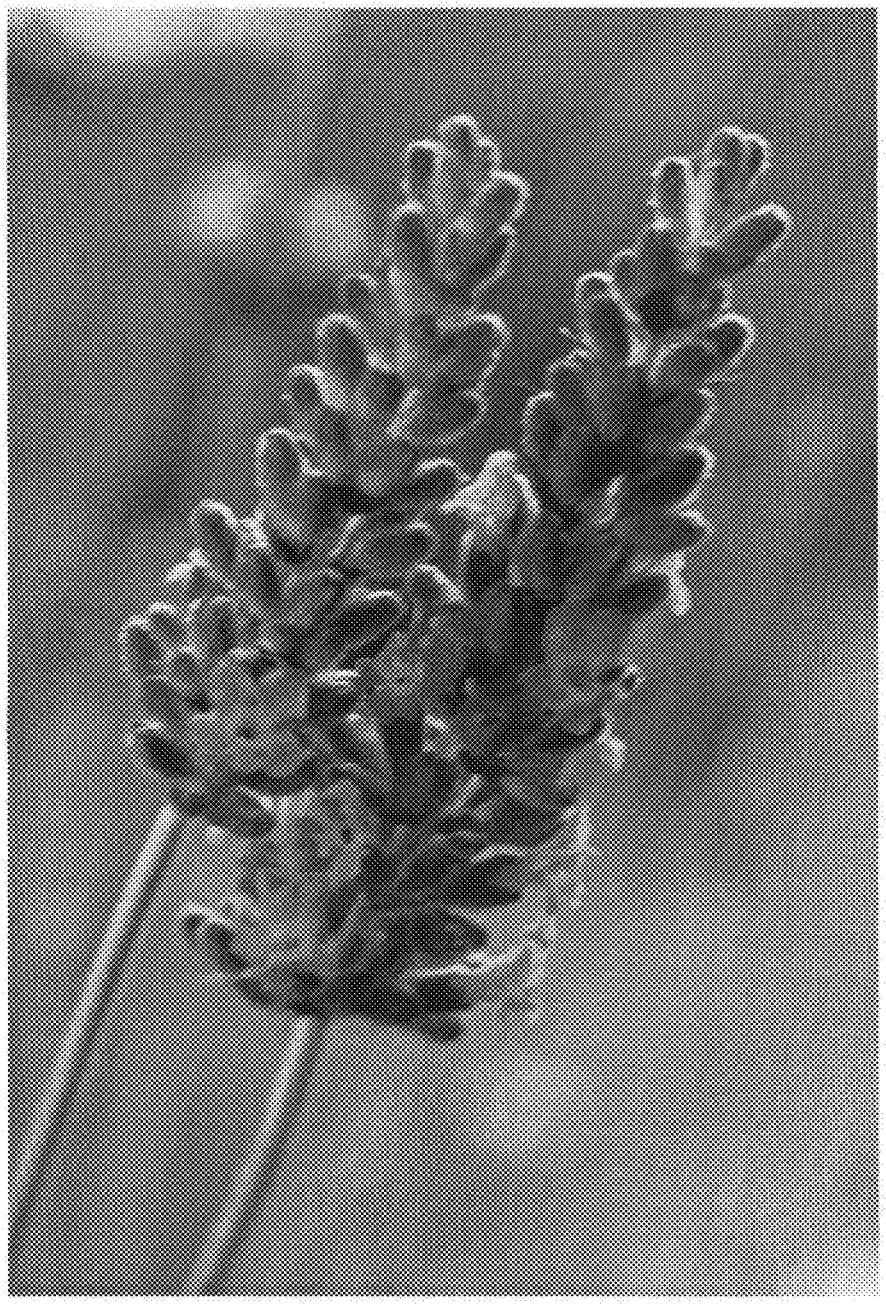

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'DOWPHSCNT' plants grown outdoors in a clay loam soil in Kent, England. The growing temperature ranged from approximately 8° C. to 28° C. during the day and from approximately 0° C. to 15° C. during the night. Plants were not shaded. Measurements and numerical values represent averages of typical plant types.

Botanical classification: *Lavandula* 'DOWPHSCNT'.

PROPAGATION

Time to initiate roots: About 21-28 days at temperatures of 64-75° F. (18-24° C.), rooting hormone can be used to promote early, uniform rooting.

Root description: Fibrous.

PLANT

Age of plant described: Approximately 4 years from a rooted cutting.

Plant spread: Approximately 70 to 80 cm.

Plant height: 45 to 50 cm at 2 years old, 50 to 60 cm at 4 years old.

Growth rate: Moderate.

Length of primary lateral branches: Approximately 18 cm.

Diameter of lateral branches: Average range 0.2 to 0.4 cm.

Quantity of lateral branches: About 40.

Branches:

*Color*.—Near Grey-Brown 199B.

*Texture/pubescence*.—Puberulent.

Internode length: Average range 1.0 to 4.0 cm.

FOLIAGE

Leaf:

*Arrangement*.—Whorls of leaves arranged opposite along stem.

*Quantity*.—Approximately 50 per main branch.

*Average length*.—Approximately 3.5 to 4.0 cm.

*Average width*.—Approximately 0.4 to 0.5 cm.

*Shape of blade*.—Linear.

*Apex*.—Acute.

*Base*.—Truncate.

*Attachment*.—Sessile.

*Margin*.—Entire and revolute.

*Texture of top surface*.—Felt-like indumentum.

*Texture of bottom surface*.—Felt-like indumentum.

*Pubescence*.—Slight.

*Color*.—Young foliage upper side: Near RHS Greyed-Green 191C. Young foliage under side: Near RHS Greyed-Green 191C. Mature foliage upper side: Near RHS Greyed-Green 191B. Mature foliage under side: Near RHS Greyed-Green 191B.

*Venation*.—Type: Linear, mid-vein depressed upper surface and protruding on lower surface. Venation color upper side: Indistinguishable from foliage. Venation color under side: Indistinguishable from foliage.

*Petiole*.—Not present.

*Foliage fragrance*.—Camphoraceous.

FLOWER

Bloom period: Summer.

Inflorescence:

*Form*.—Small single flowers arranged in whorls on terminal spikes.

*Florets*.—Corolla tube is 2-lipped, upper lip 2 lobed, lower lip 3 lobed.

*Size individual flowers*.—Length: Approximately 0.5 cm. Diameter: Approximately 0.3 cm.

*Inflorescence size*.—Length: Approximately 4 to 12 cm. Width: Approximately 1.5 to 2.0 cm.

*Coloration of corolla*.—Immature: Near RHS Violet 86B. Mature: Near RHS Violet 86B. Fading: Near RHS Violet 86B.

*Coloration of calyx*.—Immature: Near RHS Violet 83A. Mature: Near RHS Violet 83A. Fading: Near RHS Violet 83A.

*Bracteoles*.—Length: Approximately 0.4 cm.

Fragrance: Strong lavender scent.

Peduncle:

*Peduncle length*.—Average range 25 to 30 cm.

*Peduncle diameter*.—Approximately 0.2 cm.

*Aspect*.—Straight.

*Color*.—Near RHS Yellow-Green group 147B.

REPRODUCTIVE ORGANS

Stamens:

*Number*.—4.

*Stamen length*.—Less than 0.2 cm.

Anthers:

*Shape*.—Reniform.

*Length*.—Approximately 0.5 mm.

*Color*.—Pale brown, too minute for an accurate measurement with R.H.S. chart.

*Pollen*.—Color: Near Yellow-Orange, too scant to measure accurately with R.H.S. chart. Quantity: Sparse.

Pistil:

*Number*.—1.

*Length*.—Approximately 0.4 cm.

*Style*.—Length: Approximately 0.6 cm. Color: Near RHS Greyed-White 156D.

*Stigma*.—Shape: Oval. Color: Near RHS Greyed-White 156D. Ovary color: Green, not accurately measured with R.H.S. chart.

OTHER CHARACTERISTICS

Seeds and fruits: Scant amount of small seeds produced. Seed size approximately 2.5 mm, colored near RHS Brown 200A.

Disease/pest resistance: Neither resistance nor susceptibility observed. *Lavandula* is not affected by many diseases and pets. However, *Botrytis* and some root rot pathogens can be diseases problems, especially in overly wet conditions. Various species of White Fly may infect *Lavandula*.

Temperature tolerance: USDA zone 5.

What is claimed is:

1. A new and distinct cultivar of *Lavandula* plant named 'DOWPHSCNT' as herein illustrated and described.

* * * * *